US008652330B2

(12) United States Patent
Cheng et al.

(10) Patent No.: US 8,652,330 B2
(45) Date of Patent: Feb. 18, 2014

(54) ASYMMETRIC POROUS ADSORPTIVE BEAD

(75) Inventors: Kwok-Shun Cheng, Nashua, NH (US); Senthilkumar Ramaswamy, Nashua, NH (US); Chen Wang, Acton, MA (US); Nanying Bian, Nashua, NH (US); Brian Gagnon, Billerica, MA (US); Joaquin A. Umana, Stoneham, MA (US); Dennis Aquino, Chelmsford, MA (US); Neil Soice, Amherst, NH (US); Andrew Lyddiatt, Co Durham (GB)

(73) Assignee: EMD Millipore Corporation, Billerica, MA (US)

( * ) Notice: Subject to any disclaimer, the term of this patent is extended or adjusted under 35 U.S.C. 154(b) by 1023 days.

(21) Appl. No.: 12/660,715

(22) Filed: Mar. 2, 2010

(65) Prior Publication Data

US 2010/0174051 A1 Jul. 8, 2010

Related U.S. Application Data

(62) Division of application No. 11/520,848, filed on Sep. 13, 2006, now Pat. No. 7,678,269.

(60) Provisional application No. 60/718,469, filed on Sep. 19, 2005.

(51) Int. Cl.
*B01D 15/08* (2006.01)

(52) U.S. Cl.
USPC ..... 210/635; 210/656; 210/198.2; 210/502.1; 530/387.1; 530/413; 530/417

(58) Field of Classification Search
USPC ............ 210/635, 656, 198.2, 502.1; 502/404; 530/387.1, 413, 417
See application file for complete search history.

(56) References Cited

U.S. PATENT DOCUMENTS

| 4,160,728 A | 7/1979 | Kirkland et al. |
| 4,606,825 A | 8/1986 | Crane et al. |
| 4,732,811 A | 3/1988 | Margel |
| 4,971,833 A | 11/1990 | Larsson et al. |
| 5,135,650 A | 8/1992 | Hjerten et al. |

(Continued)

FOREIGN PATENT DOCUMENTS

| EP | 0266580 A2 | 5/1988 |
| FR | 2541593 A1 | 8/1984 |

(Continued)

OTHER PUBLICATIONS

Partial European Search Report EP 1764152 A1.

(Continued)

*Primary Examiner* — Ernest G Therkorn
(74) *Attorney, Agent, or Firm* — EMD Millipore Corporation

(57) ABSTRACT

The present invention relates to an asymmetric chromatography media suitable for separations applications, particularly as packed bed, fluidized bed or magnetized bed chromatography media. In certain embodiments, the asymmetric chromatography media comprises asymmetric particles, preferably beads, having at least two distinct, controlled pore size distributions. Preferably one of the distinct pore size distributions is in an internal region of the particle, and the other is in an external region or coating on the particle. These distinct pore size distributions can be modified with uniform or alternatively unique functional groups or mixtures of functional groups. The present invention allows for the control over pore size distribution within an asymmetric porous particle by providing a distinct internal region, preferably in the form of a bead, and a distinct external region, preferably in the form of a coating on the bead.

8 Claims, 2 Drawing Sheets

(56) References Cited

U.S. PATENT DOCUMENTS

| | | | |
|---|---|---|---|
| 5,312,571 | A | 5/1994 | Pujari et al. |
| 5,522,994 | A | 6/1996 | Frechet et al. |
| 5,723,601 | A | 3/1998 | Larsson |
| 5,866,006 | A | 2/1999 | Lihme et al. |
| 5,888,497 | A | 3/1999 | Jain et al. |
| 6,197,599 | B1 | 3/2001 | Chin et al. |
| 6,339,039 | B1 | 1/2002 | Porath et al. |
| 6,428,707 | B1 | 8/2002 | Berg et al. |
| 6,590,096 | B1 | 7/2003 | Berg et al. |
| 6,841,097 | B2 | 1/2005 | Andersson et al. |
| 7,678,269 | B2 | 3/2010 | Chen et al. |
| 2004/0007530 | A1 | 1/2004 | McNeff et al. |
| 2005/0053586 | A1 | 3/2005 | Conn et al. |
| 2005/0077221 | A1 | 4/2005 | Berg et al. |

FOREIGN PATENT DOCUMENTS

| | | |
|---|---|---|
| WO | WO 93/19115 A1 | 9/1993 |
| WO | WO 00/17257 A1 | 3/2000 |
| WO | WO 01/67105 | 9/2001 |
| WO | WO 03/072752 | 9/2003 |
| WO | WO 2004/070026 A1 | 8/2004 |

OTHER PUBLICATIONS

Malm et al., "A method suitable for the isolation of monoclonal antibodies from large volumes of serum-containing hybridoma cell culture supernatants", Journal of Immunological Methods, vol. 104, 1987, pp. 103-109.

European Search Report received for European Patent Application No. 10178651.5, issued on Dec. 16, 2010, 5 pages.

Mu Y et al: "Manufacture by water/oil emulsification of porous agarose beads: Effect of processing conditions on mean particle size, size distribution and mechanical properties," Chemical Engineering and Processing, Elsevier Sequoia, Lausanne, CH, vol. 44, No. 10, May 25, 2005, pp. 1157-1166, XP004922717 ISSN: 0255-2701.

Porath, Jerker and Janson, Jan-Christer and Laas, Torgny, *Journal of Chromatography*, 60 (1971) p. 167-177.

Partial European Search Report EP 1764151 A1, Dec. 15, 2006.

Partial European Search Report EP 1764152 A1, Dec. 15, 2006.

Jahanshahi, M. et al., "Subtractive chromatography for purification and recovery of nano-bioproducts", IEEE Proc._Nanobiotechnol., 152(3) pp. 121-126, Jun. 2005.

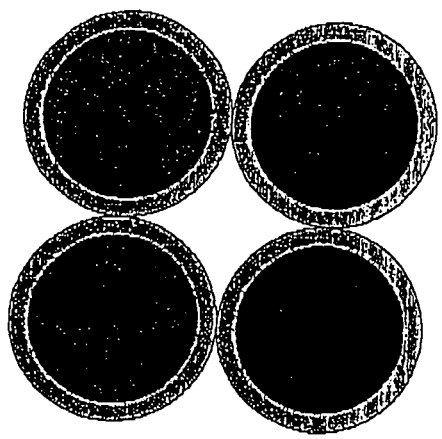 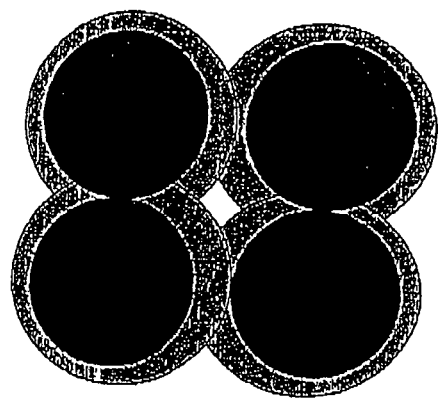
Figure 2A                    Figure 2B

ASYMMETRIC POROUS ADSORPTIVE BEAD

CROSS REFERENCE RELATED APPLICATIONS

The present utility patent application is a divisional patent application of U.S. patent application Ser. No. 11/520,848, filed on Sep. 13, 2006, projected U.S. Pat. No. 7,678,269, projected Issue Date of Mar. 16, 2010, which claims the benefit of priority of U.S. Provisional Patent Application No. 60/718,469, filed on Sep. 19, 2005, the entire content of each of which is incorporated herein in its entirety.

BACKGROUND OF THE INVENTION

The present invention relates to asymmetric porous beads suitable for chromatographic use.

Biomolecules such as proteins, polypeptides and fragments of biomolecules have become important agents for pharmaceutical and diagnostic applications. Currently, the purification of biomolecules often involves multiple steps, including chromatography. The synthesis and use of porous chromatography media for biomolecule separations is well documented. Often the chromatographic steps are performed using packed beds of beads in which a product or impurity is separated from the feed stream. These beads are generally a base matrix (such as a polysaccharide, synthetic polymer or material, ceramic, glass or a composite of the foregoing) that contains or has been modified with functionality that interacts with the biomolecule via chemical or physical means; it provides a "driving force" for binding or interaction. This complex set of interactions contributes to how the media performs in the desired separation. The ability of the media to affect a given separation between biomolecules is often referred to as the "media's selectivity". Typically these matrices exhibit porosity that allows for the biomolecule of interest to access the internal volume of the particle. This internal porosity is uniform through the particle.

Chromatographic separations typically are carried out in columns packed with the separation matrix in form of particulate beads. The size of the media particles dictates the kinetics of the separation, but smaller particles can result in high back pressure. To be able to separate large molecules the particles should have large pores, but large pores reduce the mechanical stability of the particles, particularly with polysaccharides such as agarose. Polysaccharides are advantageous because they are typically low protein binding, easy to functionalize, and can form porous structures. Conventionally, polysaccharide beads are typically made from one polysaccharide with a uniform or "symmetric" pore structure throughout the bead. Examples of these "symmetric" beads include Cellufine® (cellulose), Sepharose® (agarose) and Sephadex® (dextran). These symmetric beads bind molecules throughout the internal structure of the bead. The chemical environment (pore size, hydrophobicity, ligand type and ligand density) are essentially uniform within the internal structure. Therefore, the nature of the binding environment throughout the bead is uniform. In these systems, the driving force for separation comes from the difference in binding strength between absorbed biomolecules. Typically when a symmetric resin is used, optimization of the binding strength through control of the buffer conditions is the only driving force for achieving the desired separation. In addition, polysaccharide materials are inherently compressible, and often require chemical modification to reduce compressibility such as through crosslinking.

Another property of a symmetric resin is the mechanical strength of the media, which is a result of the material, pore structure and chemical modification. Typically for polysaccharides, the smaller the pore size of the media, the greater the mechanical strength due to higher concentration of solid material (lower porosity). However, the smaller the pore size, the more hindered the mass transfer of larger species (such as IgG) in to the adsorbent. Therefore, symmetric media design often involves the optimization/trade-off of particle rigidity and biomolecule mass transfer. This optimization problem is further complicated by the fact that the permeability of a symmetric bead is the result of the size and size distribution of the particle. As the particle size gets smaller, external particle surface area increases and therefore so does mass transfer. During elution, the smaller particle allows for a shorter diffusion time out of the media, thus causing a more concentrated, narrow elution peak. However, this improvement of the mass transfer is at the expense of permeability, which restricts column dimensions and media throughput.

In many biomolecule separations, the species of interest (target molecule) is the most concentrated species in the feedstock. In other words, the impurities are only a small percentage of the total mixture to be separated. With symmetric chromatography media, the separation is often affected by binding the target molecule and some of the impurities, and then separating the impurity by using the elution condition to differentiate the species. If the two species are very similar in their binding strength to the media, even if the proteins are different in size, the separation can be very difficult. In some cases, the difficult nature of the separation is the result of the limited number of driving forces affecting the purification. The end result is either a lower yield of purified protein from incomplete separation or that another chromatography step is then essential to further purify the target molecule using a different media with different driving forces for separation. This is time-consuming, inefficient and expensive.

Filled polysaccharide beads are well established for uses including expanded bed or fluidized bead chromatography. Typically, these materials are made by adding a solid or non-porous sphere to the polysaccharide (typically agarose) during bead formation. In this manner, a bead with one or more non-porous particles encapsulated inside the polysaccharide material can be formed. Another common technique is to coat the solid particle with a material that eventually becomes the absorbent. The solid particle serves no function in the protein capacity or separation properties of the bead. The particle typically acts only to modify the density of the bead such that the material can be used for non-packed bed applications. In some cases the solid particle provides rigidity and/or reduced gel volume.

Recently, materials have been developed with so-called "lids" or an outer layer of non-absorptive polysaccharide used to restrict the entrance to the porous structure, in order to avoid the binding of large molecules while maintaining capacity for smaller species. These materials have very low capacities for larger molecules as their internal surface area is not available to both species for binding.

Previous work has shown it possible to modify a symmetric polysaccharide structure with a chemical modification in an asymmetric way. This technique allows for the creation of a changing chemical environment within the bead. Typically the modification is used to provide a neutral layer on the outside of the bead. This prevents fouling of the outside of the bead, especially in dirty feed streams such as those found in expanded bed absorption (EBA). However, this technique does not change the pore size of the bead, therefore resulting in a symmetric pore size throughout the bead.

Methods also have been developed to modify the pore size of porous chromatography media. Using these techniques, the creation of a bimodal distribution of pore sizes is possible. However, this pore structure is evenly distributed throughout the bead and therefore does not create chemically unique regions within the bead to tune/alter observed selectivity.

Accordingly, a better media design is needed to improve biomolecule purifications in which the separation is driven by more than one characteristic of the biomolecule.

SUMMARY OF THE INVENTION

The problems of the prior art have been overcome by the present invention, which provides an asymmetric chromatography media suitable for separations applications, particularly as packed bed, fluidized bed or magnetized bed chromatography media. In certain embodiments, the asymmetric chromatography media comprises asymmetric particles, preferably beads, having at least two distinct layers, generally with each having distinct controlled pore size distributions. Preferably one of the distinct pore size distributions is in an internal region of the particle, and the other is in an external region or coating on the particle. These distinct pore size distributions can be modified with uniform or alternatively unique functional groups or mixtures of functional groups. The present invention allows for the control over pore size distribution within an asymmetric porous particle by providing a distinct internal region, preferably in the form of a bead, and a distinct external region, preferably in the form of a coating on the bead.

The asymmetric beads in accordance with the present invention provide rigidity and allow for control of the mass transfer path of packed-bed media. A rigid media can be stacked higher, thus attaining an overall higher absorbing or exchanging capacity for the column. By shortening the diffusion path, the gel can be utilized at a much higher efficiency than homogeneous beads. Under certain operating conditions, cored beads can result in sharper elution peaks and less buffer consumption.

Another aspect of this invention is the ability to have a bead with two distinct regions, each having one or more characteristics that is different from the other. For example, it may simply be pore size that differs between the first and second region. Alternatively and/or additionally, it may be ligand type, density or mixture, media material and/or percentage of agarose used in each region (when making an agarose bead) and the like that differs.

Another application of the cored beads of the present invention is in fluidized bed chromatography or magnetic chromatography where the core provides the required density (for fluidized beds) or the magnetic properties for the magnetized chromatography.

BRIEF DESCRIPTION OF THE DRAWINGS

FIG. 2A is a schematic view of an array of asymmetrical beads in accordance with an embodiment of the present invention under low stress.

FIG. 2B is a schematic view of an array of asymmetrical beads in accordance with an embodiment of the present invention under high stress.

DETAILED DESCRIPTION OF THE INVENTION

Figure 1A:
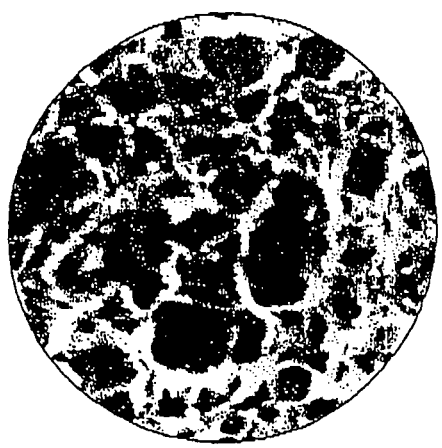
FIG. 1A is a cross-sectional view of a symmetric agarose bead.
Figure 1B:
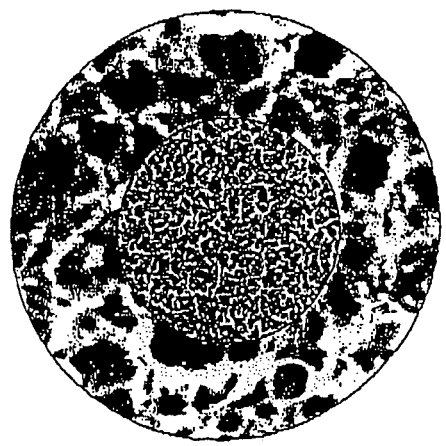
FIG. 1B is a cross-sectional view of an asymmetric agarose bead.

The asymmetric chromatographic media in accordance with the present invention enable the tuning of the mechanical and selectivity properties of the media to provide improved materials particularly suited for biomolecule separations. In a preferred embodiment, the media includes two distinct, controlled pore size distributions with unique chemical modification to each pore size region. One distinct pore size distribution is located in an internal region of media, and the other is located at an external region such as a coating. Although the pore size can be the same in both regions, yielding a symmetric chromatographic media with regionally different chemical modification, preferably the pore sizes in the two regions are different. Most preferably, the pore size in the internal region is smaller than the pore size in the external region. The size of the pores is not particularly limited; for example, the internal pore size can be small enough to effectively only adsorb small biomolecules (e.g., less than 10 KD molecular weight) or can be open enough for large biomolecules. The internal and external pore sizes can extend over a range necessary to affect an improved chromatographic separation.

Suitable media materials include those typically used for chromatographic beads, including glass, and natural and synthetic polymers such as styrene-divinyl benzene copolymer, agarose, agarose derivatives, agar, alginate, cellulose, cellulose derivatives, dextran, starch, carrageenan, guar gum, gum arabic, gum ghatti, gum tragacanth, karaya gum, locust bean gum, xanthan gum, pectins, mucins, heparins, and gelatins. Agarose is particularly preferred. The beads can be formed of the same material throughout, or can be a composite of two or more materials, preferably porous materials. For example, the bead can comprise a glass or synthetic polymer bead or core on the inside and an agarose layer on the outside. Filler may be included to control density, for example. Where agarose is the media material in both the internal and external regions, the pore size distribution can be controlled by varying the concentration of agarose. For example, a larger concentration of agarose will result in a smaller pore size, and thus the internal region can be 15% agarose while the external coating layer can be 6% agarose. Such an external layer will therefore adsorb large proteins, such as IgG, while the internal core layer effectively (within the time scales of the chromatographic separation) excludes large proteins.

More specifically, the cores of the particles of the present invention can be made of any material that is useful in chromatography. For example, the core may be a crossed linked agarose bead, a plastic, metal, glass or ceramic. Preferably when the finished bead is to have high rigidity, the core is selected from a material that is doesn't melt at the temperatures used in the manufacturing process and which is self-supportive. Suitable materials include but are not limited to plastics such as polystyrene, polyethylene, polypropylene, blends of polyethylene and polypropylene, multilayered polyethylene/polypropylene beads, acrylics, polysulfones, polyethersulfones, PVDF or PTFE; glass such as borosilicate glass, alkali resistant glass and controlled pore glass, metals such as stainless steel, nickel, titanium, palladium and cobalt or various iron, iron containing or other magnetized metals alloys and blends; and ceramics, such as silicate materials, zirconia and various ceramic blends.

The cores are preferably of a generally spherical or irregular particulate shape. Their diameter depends upon the size of bead one desires but preferably is from about 30 microns to about 150 microns in diameter.

As is common in agarose bead manufacture, various additives can be used to enhance production or add a property to the beads. One class of additives comprises volatile organics, miscible with the solution. Examples are monohydric alcohols such as methanol, ethanol, and propanols. These can be used up to concentrations that give a slightly cloudy solution.

Miscible ketones such as acetone can also be used, but care must be used as the solubility of agarose is less in ketone-water mixtures. Any mixture of two or more of these materials is also contemplated.

A further class of additives comprises non-volatile miscible organics. Non-limiting examples of these included glycerine, ethylene glycol, methyl pentane diol, diethylene glycol, propylene glycol, triethylene glycol, the methyl, ethyl, or n-butyl ethers of ethylene glycol, the dimethyl or diethyl ethers of ethylene glycol, ethylene glycol dimethyl ether acetate ethylene glycol diethyl ether acetate, diethylene glycol methyl ether, diethylene glycol ethyl ether, diethylene glycol n-butyl ether, diethylene glycol dimethyl ether, diethylene glycol diethyl ether, diethylene glycol dimethyl ether acetate, diethylene glycol diethyl ether acetate, N-methyl morpholine, N-ethyl morpholine, and the like. Polyethylene glycols of low molecular weight are also examples of materials that are in this class. Any mixture of two or more of these materials is also contemplated.

Another class of additives comprises water-soluble polymers, which include by way of examples, polyvinyl pyrrolidone, polyvinyl alcohol, polyethylene glycols, dextrans, and water-soluble polyacylamides, including substituted polyacylamides, such as polydimethylacrylamide These polymeric additives can be used as blends with the agarose in the initial dissolution step, or they can be dissolved in the solution after the addition and dissolution of the agarose. Care must be taken not to add an excessive amount of polymer, as coagulation of the solution may occur. Ratios of polymer to agarose of from about 0.1 to 10 are possible. Preferred polymers are polyvinyl alcohol, dextrans and polyacrylamides.

The media, particularly where comprised of agarose, may be crosslinked if desired by any of the chemistries commonly used in the industry to crosslink materials containing multiple hydroxyl groups, such as polysaccharide beads, these chemistries being as non-limiting examples, epichlorohydrin or other multifunctional epoxy compounds, various bromyl chemistries or other multifunctional halides; formaldehyde, gluteraldehyde and other multifunctional aldehydes, bis(2-hydroxy ethyl)sulfone, dimethyldichloro-silane, dimethylolurea, dimethylol ethylene urea, diisocyanates or polyisocyanates and the like.

It may also have one or more functionalities applied to it, including ligands, such as Protein A or Protein G, natural or recombinatorily derived versions of either, modified versions of protein A or G to render them more caustic stable and the like, various chemical ligands such as 2-aminobenzimidazole (ABI), aminomethylbenzimidazole (AMBI), mercaptoethylpyridine (MEP) or mercaptobenzimidazole (MBI), or various chemistries that render the agarose cationic, anionic, philic, phobic or charged, as is well-known in the art of media formation.

Functional groups used in liquid chromatography that are adaptable to the present invention include groups such as, but not limited to, ion exchange, bioaffinity, hydrophobic, groups useful for covalent chromatography, thiophilic interaction groups, chelate or chelating, groups having so called pi-pi interactions with target compounds, hydrogen bonding, hydrophilic, etc.

These groups may be added after the agarose bead has been formed and crosslinked or they may be added to the initial solution and the composition of the initial solution is modified accordingly, such as pH being lowered or raised, so that the reaction to link the functional groups to the agarose occurs concurrently with the crosslinking reaction.

These functionalities are commonly applied in two ways. First these functionalities can be applied with the addition of an electrophile-containing molecule which possesses the desired functional group or a precursor thereof. Typically, the hydroxyl containing base matrix is activated with sodium hydroxide, which allows for efficient reaction of the base matrix with the aforementioned electrophile. Non-limiting examples include: bromopropane sulfonic acid, propane sultone, allyl glycidyl ether, allyl bromine, glycidyl trimethylammonium chloride, butanediol diglycidyl ether, sodium chloroacetate. Alternatively, a nucleophilic group, such as an amine or thiol, can be added to the base matrix using methods known in the art and then the above electrophilic reagents can be used to modify the base matrix. Secondly, these functionalities can be applied with activation of the base matrix with an electrophilic group including the following non-limiting samples, cyanogen bromide, activated carboxylic acids, aldehydes, esters, epoxides such as butanediol diglycidyl ether, epichlorohydrin, allyl bromide and allyl glycidyl ether, followed by reaction of the activated base matrix with the appropriate nucleophilic molecule containing the functionality of choice. These nucleophiles can be small molecules such as aminopropane sulfonic acid or larger entities such as polyethyleneimine or proteins and peptides. In addition, all the above chemistries can be added to the bead after hydrophilic spacer arms or "tentacles" such as dextran have been attached to the base matrix. This provides additional surface area for binding and further changes the pore size and chemical environment within the bead's asymmetric structure.

The asymmetric chromatography media of the present invention offer improved mechanical properties over symmetric beads. Many common chromatography media formed from polysaccharides are compressible. This compressibility is initially determined by the porosity of the material. For example, commercial agarose beads are typically 4-6% agarose, which means that the particles are 96-94% porous. Without chemical modification, these materials have very limited chromatographic applications. Although after extensive crosslinking, these materials can be rigid enough for many applications, the more porous the initial polysaccharide bead, the more limited its mechanical properties will be. With the asymmetric media of the present invention, if the internal bead is much less porous than the external pore structure, the mechanical properties of the internal region is much greater than that of the external region. Under mechanical stress, the external region will compress much like its symmetric counterparts, However, after the initial compression, the internal regions of adjacent beads will begin to contact each other, as shown diagrammatically in FIG. 2. This "point contact" of the internal regions leads to a packed bed with the mechanical compressibility of the internal bead structure. Because this internal structure can be less porous and more rigid, the net effect is a more porous or open external structure with the bed mechanical compressibility of a much more rigid material. If an incompressible material is used as the internal pore structure, then the resulting chromatography bed will be incompressible after "point contact" of the internal structures.

The selectivity of chromatography media for a given biomolecule or mixture thereof, is governed by a complex set of factors including ligand type, ligand density, media pore size, media hydrophobicity, etc. The selectivity of a symmetric bead could be viewed as "one dimensional" because the binding environment in the bead is uniform. Therefore, the selectivity of the media is driven by the ability of each individual biomolecule to interact within the same binding environment. In other words, "molecule specific interactions" (species net charge, hydrophobicity, hydrogen bonding, etc.), not molecular size, drive the separation of the different biomolecules. An advantage of an asymmetric chromatography bead is that the material contains at least two distinct chemical/binding environments in which species can bind. This structure can be created by varying 1) the pore size between the internal and external pore structures, 2) the ligand type, ligand density and/or ligand mixture, 3) media material (e.g. more philic outside/more phobic inside), and combinations of 1), 2) and 3). These materials provide "two dimensional" selectivity, because the separation is driven not only by the molecule specific interactions, but also by the at least two distinct regions within the media. For example, a weaker binding species will likely concentrate in a stronger binding environment or larger species could be excluded from the internal pore structure.

A specific example of an application of the novel media of the present invention is the separation of a Mab from host cell proteins (HCP). Mab's are higher molecular weight proteins (160 kD) and cannot easily diffuse in 15% agarose gels. Accordingly, a 6% agarose bead with an internal bead of 15% agarose provides an impurity "sink" in which HCP can be adsorbed to one region (with a possibly unique chemical modification) while the Mab would be absorbed to the 6% structure. This provides enhanced removal of common HCP impurity. In order to maximize the binding capacity of the desired protein (Mab), the smaller pore size region (the sink region) can be minimized to 20% of the total volume and the more open pore region of the agarose bead can be modified with "tentacles" of a hydrophilic ligand carrier such as dextran. This can double the capacity of the agarose bead for Mab.

Another advantage is the external region can be limited in thickness (1-15 microns) to allow for a shorter diffusional path during elution. This can provide a more narrow elution peak and possibly better resolution.

A suitable process for making the media of the present invention involves dissolving/melting the media material, such as agarose, in a suitable liquid, adding cores, preferably in bead form, so that the cores are coated with the agarose, mixing the coated cores with a hydrophobic liquid to form an emulsion and maintaining that emulsion at a temperature equal to or greater than the melting point of the agarose, passing it through a static mixer to create agarose droplets and solidifying the agarose droplets in a second bath of hydrophobic liquid. The beads can then be washed and used or further processed to crosslink the agarose and/or add various functionalities onto the agarose as is known in the art.

EXAMPLES

Example 1A

Asymmetric Agarose Bead with Unique Chemical Environments and Uniform Pore Size

SP-Sepharose Fast Flow (6% crosslinked agarose) was coated with a 10-15 micron layer of 6% agarose according to the following method: 50 ml of the beads were then mixed into 300 ml of 6% agarose solution (D-5 Agarose from Hispanagar) to obtain a slurry. The agarose-beads mixture was added to 1000 ml of mineral oil at 90° C. under constant agitation to obtain an emulsion in which the oil phase is continuous. The emulsion was then pumped through a 0.5 inch (12.7 mm) diameter, 6 inches (152.4 mm) long Kenics static mixer (KMR-SAN-12) at a flow rate of 3 L/min into mineral oil at 5° C. The resulting agarose beads had an estimated external layer thickness of 10 um and the bead population was predominantly single-cored (>50%). The beads were settled, washed with water, ethanol and then water. The beads were crosslinked according to the method disclosed in Porath, Jerker and Janson, Jan-Christer and Laas, Torgny, *Journal of Chromatography*, 60 (1971) P. 167-177, the disclosure of which is hereby incorporated by reference. The bead was then modified with bromoporane sulphonic acid (BPSA). In a jar, 10 g beads, 30 ml of 5M NaOH, 7.2 g BPSA were added and agitated overnight at 50° C. The beads were washed with 500 ml of Milli-Q quality water and the BPSA process was repeated at second time. The beads were washed with 500 ml of Milli-Q water and then stored in 20% ethanol.

Example 1B

SP-Sepharose Fast Flow (6% crosslinked agarose) was coated with a 10-15 micron layer of 6% agarose as discussed in Example 1A. The beads were crosslinked according to the method disclosed in Porath, Jerker and Janson, Jan-Christer and Laas, Torgny, *Journal of Chromatography*, 60 (1971) P. 167-177. The bead was then modified with bromoporane sulphonic acid (BPSA). In a jar, 10 g beads, 30 ml of 5M NaOH, 7.2 g BPSA were added and agitated overnight at 50° C. The beads were washed with 500 ml of Milli-Q quality water and the BPSA process was repeated three additional times. The beads were washed with 500 ml of Milli-Q water and then stored in 20% ethanol.

Example 1C.

SP-Sepharose Fast Flow (6% crosslinked agarose) was coated with a 10-15 micron layer of 6% agarose as discussed in Example 1A. The beads were crosslinked according to the method disclosed in Porath, Jerker and Janson, Jan-Christer and Laas, Torgny, *Journal of Chromatography*, 60 (1971) P. 167-177. The bead was then modified with allyl glycidyl ether (AGE). In a jar, 10 g beads, 10 ml of 8M NaOH, 2 g AGE, 2 g $Na_2SO_4$ were added and agitated overnight at 25° C. The beads were washed with 500 ml of Milli-Q quality water and then stored in 20% ethanol.

Selectivity Testing

Two proteins of different net charge and molecular weight were used to test the nature of the selectivity or separation factor under typical cation exchange (CEX) conditions. Pulses of a protein mixture containing 0.5 mg/ml polyclonal IgG (Sigma) and 0.5 mg/ml lysozyme (Sigma) in 50 mM acetate buffer with NaCl to give conductivity 10 mS at pH 4.5 were applied to each sample column at 200 cm/hr (7 cm bed height, 0.66 cm diameter). The pulse was then eluted at 200 cm/hr using a 20 CV NaCl gradient starting at 10 mS and ending at 80 mS. The peak for each protein was recorded in terms of column volumes (CV) from the start of the elution gradient (dead volume was corrected). The data for the peak separation are shown in Table 1:

TABLE 1

| SAMPLE | IgG PEAK (CV) | LYSOZYME PEAK (CV) | PEAK SEPARATION (CV) |
|---|---|---|---|
| Example 1A | 9.36 | 13.46 | 4.1 |
| Example 1B | 9.63 | 14.03 | 4.4 |
| Example 1C | 9.95 | 13.65 | 3.7 |
| SP-Sepharose Fast Flow | 9.95 | 13.85 | 3.9 |

The Table reports the peak positions in the elution gradient for both IgG and lysozyme. The longer the delay in elution (greater CV), the more strongly bound a species is to the media. The media were designed to have differing chemical environments, mainly the density of sulfopropyl ligands. The difference in ligand density between the outside agarose region and the internal region is increasing in the following order: Example 1C<Example 1B<Example 1A. There is very little difference between the inside ligand density and outside ligand density in Example 1C, each having essentially identical chemistry. The IgG peak position follows this general trend. The IgG peak elution occurs first for the bead with the lowest ligand density in the outer layer, while for Example 1C the elution occurs identically to the internal bead structure alone (SP-Sepharose control). Interestingly, the lysozyme and peak separation do not show the same simple trend. However, it is clear that the peak separation is greater for the asymmetric beads with unique chemical regions within the bead structure.

Example 2

Agarose beads (ABT Technologies) containing 10% agarose were crosslinked according to Porath, et al., above. The bead was then modified with bromopropane sulphonic acid (BPSA). In a jar, 100 g beads, 300 ml of 5M NaOH, 72 g BPSA were added and agitated overnight at 50° C. The beads were washed with 1500 ml of Milli-Q quality water and the BPSA process was repeated two more times. The beads were washed with 1500 ml of Milli-Q water and then stored in 20% ethanol. The beads were then coated with a layer of 6% agarose to form asymmetric agarose beads according to the following method: 100 ml of the beads were then mixed into 600 ml of 6% agarose solution (D-5 Agarose from Hispanagar) to obtain a slurry. The agarose-beads mixture was added to 2000 ml of mineral oil at 90° C. under constant agitation to obtain an emulsion in which the oil phase is continuous. The emulsion was then pumped through a 0.5 inch (12.7 mm) diameter, 6 inches (152.4 mm) long Kenics static mixer (KMR-SAN-12) at a flow rate of 3 L/min into mineral oil at 5° C. The resulting agarose beads had an estimated external layer thickness of 10 um and the bead population was predominantly single-cored (>50%). The beads were settled, washed with of water, ethanol and then water. These beads were crosslinked according to Porath, et al., above. The beads were then treated with glycidyl trimethylammonium chloride (GTMAC). In a jar, 100 ml of beads were added to 100 ml of 75% GTMAC. After mixing, 3.3 ml of 50% NaOH was added and the reaction was shaken overnight at 25° C. The beads were washed with 1500 ml of Milli-Q water. The beads were then coated with again with another layer of 6% agarose. The beads were then shown a mixture of two dyes: methylene blue (1 mg/ml) and ponceau S (1 mg.ml), in Milli-Q water. A sample of beads was shown only methylene blue as a control. The beads were washed with Milli-Q water three times (100 ml). The dye location was recorded using a digital camera adapted to a microscope lens.

The BPSA (negative charge) center 10% agarose region bound methylene blue dye. The second region is positively charged (with GTMAC) and did not bind methylene blue. However, upon exposure of the bead to a mixture of methylene blue and the negatively charged dye ponceau S (red color), a blue center region was observed with a strong band of red where the GTMAC region is. The neutral outermost region contained some residual red dye from incomplete washing, but was less intense red as expected.

Example 3

Example 3A

Asymmetric Agarose Bead with Unique Chemical Environments and Two Distinct Pore Size Regions: Preparation of Internal Structure A 15% agarose bead was made using the following method: 1000 ml of 15% agarose solution (D-5 Agarose from Hispanagar) was added to 2000 ml of mineral oil containing 120 ml of Span 80 emulsifier in a first oil bath at 80° C. under constant agitation to obtain an emulsion in which the oil phase is continuous. The emulsion was then pumped through a 0.5 inch (12.7 mm) diameter, 6 inches (152.4 mm) long Kenics static mixer (KMR-SAN-12) at a flow rate of 3 L/min into a second bath of mineral oil at 5° C. Spherical homogeneous agarose beads were obtained with a largest particle diameter of 200 um. The beads were settled, washed with of water, ethanol and then water and sieved to yield a bead size range of 75-125 ☐m. The beads were then crosslinked according to the method disclosed in Porath, Jerker and Janson, Jan-Christer and Laas, Torgny, *Journal of Chromatography*, 60 (1971) P. 167-177, the disclosure of which is hereby incorporated by reference. The beads were then modified with allyl glycidyl ether (AGE). In a jar, 120 g beads, 150 ml of 8M NaOH, 30 g sodium sulfate and 100 g of AGE were added and agitated overnight at 45° C. The beads were washed with 3×500 ml of Milli-Q quality water.

Example 3B

Asymmetric Agarose Bead with Unique Chemical Environments and Two Distinct Pore Size Regions: Preparation of Internal Structure A portion of the beads made in Example 3A were modified to create a cation exchange material. The beads were modified with sodium meta-bisulfite. In a jar, 60 g beads, 47 ml of Milli-Q water, 7.9 g of 50% wt NaOH and 23.4 g sodium meta-bisulfite were added and agitated overnight at room temperature. The beads were washed with 3×500 ml of Milli-Q quality water.

Example 3C

Asymmetric Agarose Bead with Unique Chemical Environments and Two Distinct Pore Size Regions: Preparation of External Structure The beads from Example 3B were coated with 6% agarose according to the following method: 50 ml of the beads were then mixed into 300 ml of 6% agarose solution (D-5 Agarose from Hispanagar) to obtain a slurry. The agarose-beads mixture was added to 1000 ml of mineral oil at 90° C. under constant agitation to obtain an emulsion in which the oil phase is continuous. The emulsion was then pumped through a 0.5 inch (12.7 mm) diameter, 6 inches (152.4 mm) long Kenics static mixer (KMR-SAN-12) at a flow rate of 3 L/min into mineral oil at 5° C. The resulting agarose beads had an estimated external layer thickness of 10 um and the bead population was predominantly single-cored.(>50%). The beads were settled, washed with of water, ethanol and then water and sieved to yield a bead size range of 75-1250 m. The beads were crosslinked according to the method disclosed in Porath, Jerker and Janson, Jan-Christer and Laas, Torgny, *Journal of Chromatography*, 60 (1971) P. 167-177, the disclosure of which is hereby incorporated by reference. The beads were washed with 3×500 ml of Milli-Q quality water.

Example 3D

Asymmetric Agarose Bead with Unique Chemical Environments and Two Distinct Pore Size Regions: Addition of Cation Exchange Ligands to External Structure A portion of the beads from Example 3C were then modified with bromopropane sulfonic acid (BPSA). In a jar, 10 g beads, 30 ml of 5M NaOH, 7.2 g BPSA were added and agitated overnight at 50° C. The beads were washed with 500 ml of Milli-Q quality water and then stored in 20% ethanol.

Example 3E

Asymmetric Agarose Bead with Unique Chemical Environments and Two Distinct Pore Size Regions: Addition of Cation Exchange Ligands to External Structure A portion of the beads from Example 3C were then modified with bromopropane sulfonic acid (BPSA). In a jar, 10 g beads, 30 ml of 5M NaOH, 7.2 g BPSA were added and agitated overnight at 50° C. The beads were washed with 500 ml of Milli-Q quality water and the BPSA process was repeated one additional time. The beads were washed with 500 ml of Milli-Q water and then stored in 20% ethanol.

Example 3F

Asymmetric Agarose Bead with Unique Chemical Environments and Two Distinct Pore Size Regions: Addition of Cation Exchange Ligands to External Structure A portion of the beads from Example 3C were then modified with bromopropane sulfonic acid (BPSA). In a jar, 10 g beads, 30 ml of 5M NaOH, 7.2 g BPSA were added and agitated overnight at 50° C. The beads were washed with 500 ml of Milli-Q quality water and the BPSA process was repeated two additional times. The beads were washed with 500 ml of Milli-Q water and then stored in 20% ethanol.

Selectivity Testing.

Two proteins of different net charge and molecular weight were used to test the nature of the selectivity or separation factor under typical cation exchange (CEX) conditions. A mixture of a protein containing 0.5 mg/ml polyclonal IgG (Sigma) and 0.5 mg/ml lysozyme (Sigma) in 50 mM acetate buffer with NaCl to give conductivity 10 mS at pH 4.5 were applied to each sample column at 200 cm/hr (7 cm bed height, 0.66 cm diameter) such that the net protein loaded on the media was 10 mg/mL. The protein mixture was then eluted at 200 cm/hr using a 30 CV NaCl gradient starting at 10 mS and ending at 80 mS. The peak for each protein was recorded in terms of column volumes (CV) from the start of the elution gradient (dead volume was corrected). The data for the peak separation are shown in Table 2:

TABLE 2

| SAMPLE | IgG PEAK (CV) | LYSOZYME PEAK (CV) | PEAK SEPARATION (CV) |
|---|---|---|---|
| Example 3D | 19.7 | 25.7 | 6.6 |
| Example 3E | 18.6 | 26.7 | 8.1 |
| Example 3F | 18.7 | 26.8 | 8.1 |
| SP-Sepharose Fast Flow | 20.3 | 26.3 | 6 |

Table 2 reports the peak positions in the elution gradient for both IgG and lysozyme. The longer the delay in elution (greater CV), the more strongly bound a species is to the media. The media were designed to have differing chemical and physical environments, mainly the density of sulfopropyl ligands and internal structure pore size. For Example 3D, the selectivity is similar to that of a standard commercial resin (Sepharose Fast Flow). However, Examples 3E and 3F show an increased separation of the two protein peaks as a result of the asymmetric bead structure with unique chemical and pore size regions.

Example 5

Agarose Cored Bead 75 ml of 15% cross-linked agarose beads of 100 um average diameter (Made using process patent to be file on same day) was mixed with 100 ml of 4% agarose solution (Hispanagar D5) to obtain a slurry. The agarose-bead mixture was added to 2000 ml of mineral oil at 80° C. under constant agitation to obtain an emulsion in which the oil phase is continuous. The emulsion was then pumped through a 0.5" diameter, 6" long Ross ISG static mixer at a flow rate of 3 L/min into mineral oil at 5° C. The resulting asymmetric beads had an estimated external region thickness of 10 um and the bead population was predominantly single-cored. (>60%)

What is claimed is:

1. A method of separating a monoclonal antibody from a host cell protein, the method comprising contacting a mixture of antibody and host cell protein with an asymmetric chromatography particle comprising an internal region and an external region, each of the internal region and the external region has a different percent agarose, wherein the monoclonal antibody is absorbed onto the external region and the host cell protein is adsorbed onto the internal region.

2. The method of claim 1, wherein the external region comprises an agarose concentration of 6% and the internal region comprises an agarose concentration of 15%.

3. The method of claim 1, wherein the in internal region higher percentage of agarose than the external region.

4. The method of claim 1, wherein the external region comprises a thickness of 1 to 15 microns.

5. The method of claim 1, wherein the chromatography particle is modified with a hydrophilic ligand carrier.

6. The method of claim 1, wherein the chromatography particle is modified with a hydrophilic ligand carrier and the hydrophilic ligand carrier is dextran.

7. The method of claim 1 wherein the agarose of the internal and external region is crosslinked.

8. The method of claim 1 wherein the agarose of the internal and external region is crosslinked and wherein the chromatography particle is modified with a hydrophilic ligand carrier and the hydrophilic ligand carrier is dextran.

* * * * *